(12) United States Patent
Herrmann

(10) Patent No.: US 9,649,085 B2
(45) Date of Patent: May 16, 2017

(54) INDUCTIVE ROTARY JOINT WITH SECONDARY SAFETY CIRCUIT

(71) Applicant: Schleifring und Apparatebau GmbH, Fürstenfeldbruck (DE)

(72) Inventor: Ulrich Herrmann, Munich (DE)

(73) Assignee: SCHLEIFRING UND APPARATEBAU GMBH, Furstenfeldbruck (DE)

( * ) Notice: Subject to any disclaimer, the term of this patent is extended or adjusted under 35 U.S.C. 154(b) by 0 days.

(21) Appl. No.: 14/971,111

(22) Filed: Dec. 16, 2015

(65) Prior Publication Data

US 2016/0181791 A1    Jun. 23, 2016

(30) Foreign Application Priority Data

Dec. 18, 2014 (EP) ..................................... 14198958

(51) Int. Cl.

| A61B 6/03 | (2006.01) |
|---|---|
| H05G 1/10 | (2006.01) |
| H05G 1/12 | (2006.01) |
| A61B 6/00 | (2006.01) |
| H02H 7/122 | (2006.01) |
| H01F 38/14 | (2006.01) |

(Continued)

(52) U.S. Cl.
CPC ............... *A61B 6/56* (2013.01); *A61B 6/032* (2013.01); *H01F 38/14* (2013.01); *H01F 38/18* (2013.01); *H02H 7/125* (2013.01); *H02H 7/1225* (2013.01); *H02J 5/005* (2013.01); *H02J 50/10* (2016.02); *H05G 1/10* (2013.01); *H05G 1/12* (2013.01)

(58) Field of Classification Search
CPC . A61B 6/032; A61B 6/56; H05G 1/10; H05G 1/12
USPC .................................................. 378/101, 104
See application file for complete search history.

(56) References Cited

U.S. PATENT DOCUMENTS

| 5,770,936 A | 6/1998 | Hirai |
| 5,914,999 A * | 6/1999 | Beyerlein ................ H05G 1/34 378/101 |

(Continued)

FOREIGN PATENT DOCUMENTS

| EP | 14198958.2 | 12/2014 |
| JP | 62088300 | 4/1987 |

*Primary Examiner* — Allen C. Ho
(74) *Attorney, Agent, or Firm* — Yakov Sidorin; Quarles & Brady LLP

(57) ABSTRACT

An inductive rotating power transfer circuit, preferably for transferring electrical power from the stationary part to the rotating part of a CT scanner comprises an inductive power transformer having a stationary primary side and a rotating secondary side. The secondary side is connected via a rectifier to a filtering capacitor, delivering electrical power to a load. One of the output pins of the filtering capacitor is connected to a secondary ground at the rotating part which is further connected to a stationary protective ground via a galvanic slip ring. In the case of a short circuit between a secondary transformer winding and the secondary ground, the secondary winding is partially short-circuited by one of the rectifier diodes. This causes an asymmetric current load at the primary side and a current flowing through the slip ring. Both currents may be used to detect a failure of the secondary winding.

10 Claims, 9 Drawing Sheets

(51) Int. Cl.
  *H02J 5/00*     (2016.01)
  *H01F 38/18*    (2006.01)
  *H02H 7/125*    (2006.01)
  *H02J 50/10*    (2016.01)

(56) References Cited

U.S. PATENT DOCUMENTS

| | | | | |
|---|---|---|---|---|
| 5,923,721 A * | 7/1999 | Duschka | A61B 6/4429 | 378/101 |
| 5,923,723 A * | 7/1999 | Herbst | H05G 1/06 | 378/101 |
| 6,072,856 A * | 6/2000 | Van Der Broeck | H02M 3/337 | 363/132 |
| 6,298,116 B1 * | 10/2001 | Methley | H02J 7/34 | 378/101 |
| 6,563,717 B2 * | 5/2003 | Lunding | H02M 3/285 | 363/15 |
| 6,674,836 B2 * | 1/2004 | Harada | H05G 1/10 | 378/107 |
| 6,738,275 B1 * | 5/2004 | Beland | H02M 1/088 | 363/21.02 |
| 6,917,531 B2 * | 7/2005 | Scheel | H02M 7/5236 | 363/21.02 |
| 6,975,698 B2 * | 12/2005 | Katcha | H05G 1/10 | 378/101 |
| 7,050,539 B2 * | 5/2006 | Loef | H02M 3/285 | 363/15 |
| 7,054,411 B2 * | 5/2006 | Katcha | H05G 1/10 | 336/105 |
| 7,305,065 B2 * | 12/2007 | Takahashi | H05G 1/12 | 378/101 |
| 7,327,827 B2 * | 2/2008 | Sakamoto | H05G 1/12 | 378/101 |
| 7,397,896 B2 * | 7/2008 | Beyerlein | H05G 1/10 | 378/101 |
| 7,400,708 B2 * | 7/2008 | Takahashi | H05G 1/10 | 378/101 |
| 7,717,619 B2 * | 5/2010 | Katcha | G08C 17/04 | 378/15 |
| 7,826,586 B2 * | 11/2010 | Nakayama | A61B 6/035 | 378/101 |
| 7,830,685 B2 * | 11/2010 | Wagner | H02M 3/285 | 363/17 |
| 8,155,271 B2 * | 4/2012 | Beyerlein | H05G 1/10 | 307/91 |
| 8,242,639 B2 * | 8/2012 | Krumme | A61B 6/56 | 307/104 |
| 8,249,217 B2 * | 8/2012 | Iijima | G01R 31/42 | 378/101 |
| 8,385,504 B2 * | 2/2013 | Hattrup | H02M 1/40 | 378/101 |
| 8,576,987 B2 * | 11/2013 | Fukuwara | A61B 6/4014 | 378/101 |
| 8,774,364 B2 * | 7/2014 | Aoki | H01J 35/045 | 378/104 |
| 8,861,681 B2 * | 10/2014 | Caiafa | H02M 3/337 | 378/101 |
| 9,084,335 B2 * | 7/2015 | Mekonnen | H05G 1/10 | |
| 9,119,592 B2 * | 9/2015 | Katcha | A61B 6/03 | |
| 9,186,120 B2 * | 11/2015 | Zimpfer | A61B 6/56 | |
| 9,362,047 B2 * | 6/2016 | Krumme | A61B 6/56 | |
| 2009/0185658 A1 | 7/2009 | Katcha et al. | | |
| 2011/0075796 A1 * | 3/2011 | Loef | A61B 6/56 | 378/15 |
| 2013/0214614 A1 | 8/2013 | Krumme | | |
| 2013/0340165 A1 | 12/2013 | Dong | | |
| 2015/0055750 A1 * | 2/2015 | Takahashi | H05G 1/48 | 378/62 |
| 2016/0181791 A1 | 6/2016 | Herrmann | | |
| 2016/0181825 A1 * | 6/2016 | Herrmann | H02J 5/005 | 307/104 |
| 2016/0181871 A1 * | 6/2016 | Krumme | A61B 6/03 | 307/104 |

\* cited by examiner

INDUCTIVE ROTARY JOINT WITH SECONDARY SAFETY CIRCUIT

CROSS-REFERENCE TO RELATED APPLICATION

This application claims priority from and benefit of the pending European Application No. 14198958.2 filed on Dec. 18, 2014, the disclosure of which is incorporated herein by reference.

BACKGROUND

1. Field of the Invention

The invention relates to an inductive power coupling device for coupling electrical power between two units that are rotatable against each other, and, specifically for power couplers used in computed tomography scanners. Such power couplers are also known as rotary joints.

2. Description of Relevant Art

In computed tomography (CT) scanners and other related machines high-power in the range from 10 kW up to more than 100 kW is transferred from a stationary side to a rotating side. There, a high voltage in the range of above hundred kilovolts is generated to produce x-ray radiation.

In U.S. Pat. No. 7,054,411 a multiple channel inductive rotary joint is disclosed. It has inductive channels for transferring power from the stationary side to the rotating side. There is an auxiliary power and a main power circuit. Furthermore a capacitive feedback link for power control is provided. There may be some failure states such as a short circuit of a rotating power channel to protective earth, which may cause dangerous high voltages at the rotating part and which may cause the rotating part of the feedback link to be inoperative and, therefore, may interfere with the communication to a primary power controller.

SUMMARY

The embodiments of the invention are directed to increasing the safety of devices that utilize inductive power couplers between rotating parts. Such devices may be CT scanners. Specifically, a short circuit of a rotating power channel to protective earth should no more cause excessive voltages at the rotating part. Furthermore, means and methods should be provided to detect such a short circuit from the stationary side without requiring communication from the rotating side.

Inductive rotary joints usually are built like power transformers, where one side is rotating against another side. For example, in CT scanners, power has to be transferred from the stationary to the rotating side. Therefore, the power coupler is a transformer having a stationary primary winding and a secondary rotating winding. For simplicity, the following explanations and embodiments refer to a CT scanner rotary joint. The same concepts can be applied to any rotary joint in general and furthermore to a rotary joint configured to transfer power from a rotating side to a stationary side.

As a transformer can only transfer AC (alternating current), it is either fed by an AC line voltage or by an inverter, generating an AC voltage of a higher frequency which can better be transferred via a rotating transformer. At the output side, in most cases this AC voltage is converted to a DC voltage to provide a DC output. This may be done by a bridge rectifier, followed by a filtering capacitor to generate a smooth DC voltage. Although the secondary winding of the rotating transformer and the DC voltage generated thereof are floating, there is a significant capacitance between the secondary DC circuit and the mechanical base holding the components of the rotating part. This is specifically the case with a CT scanner, with a large number of electronic components mounted to a rotating disk forming the mechanical base of the rotating part. The mechanical base is further also referred as secondary or rotating ground. Furthermore, there may be capacitors for suppressing noise, which are connected between the DC voltage supply and the mechanical base, which may further be connected by a galvanic slip ring to stationary protective earth. This connection to protective earth further prevents high voltage at the rotating part in the case of certain failures against ground, and therefore prevents electrical shock of persons operating the device when touching the device in such failure state.

Basically, the secondary winding is isolated against the mechanical parts, and therefore against the protective earth. Under certain circumstances, the isolation may fail. The applicable circumstances may include, for example, a mechanical failure due to mechanical damaging of the isolation, which may occur at ends of the isolation or at locations where the isolated wire of the secondary winding is connected to the external device, such as a rectifier. There may be other failure modes, such as thermal failures that may be caused by overheating, or electrical failures that be caused by longtime degradation of the isolation, or by sparking or arcing, or even a combination of some of these failure modes.

When such a failure of a short circuit occurs, the ground capacitor (the previously mentioned capacitance between the secondary output and the rotating ground) is connected parallel to at least one of the bridge rectifier diodes. The bridge rectifier now acts as a voltage doubler. As a consequence, the DC output voltage may become twice the normal DC output voltage. With a high probability, this will result in a failure of many of the electrical or electronic components attached to the DC output voltage.

In a first embodiment, there is a low impedance galvanic connection between a DC output line, which may either be the positive DC output or the negative DC output, and the mechanical base.

It is preferred if a galvanic connection is provided between the stationary and rotating sides which is also connected to said DC voltage output. The galvanic connection preferably is a slip ring having a brush sliding on a sliding track. In another embodiment, the galvanic connection may be made by a bearing, which for example may be a ball bearing between the rotating and the stationary parts. Most preferably, this bearing is further complemented by a parallel galvanic low current slip ring. Under normal operating conditions, there is no current flowing through the galvanic ground connection. Therefore, this galvanic ground connection has an extremely long lifetime, as there is not wear of the brushes and the sliding tracks due to arcing which usually occurs under high currents. There is also no wear or corrosion, if a bearing is used.

In a further embodiment, a control unit is provided at the primary side of the rotating transformer, which side preferably is the stationary side. This control unit preferably is measuring the current through the galvanic ground connection. In the failure case of a short circuit of the secondary winding towards the secondary ground, there will be significant ripple current flowing through this line, which can easily be detected by the control unit. This control unit may further issue an emergency switch-off signal to disable the power supply from the device. Such a signal may control a primary inverter supplying an AC voltage to the primary winding of the capacitive rotating transformer. In another embodiment, the control unit may be connected to a voltage and/or current sensor at the primary winding and/or at the primary input, detecting abnormal voltages/currents to detect said short circuit.

During standstill a ball bearing holding the rotating part may provide a sufficient grounding or protective earth. Grounding may further be increased by a grounding jumper which may be inserted manually for maintenance and service.

In a further embodiment, there may be a switch for generating a short circuit as described above, for example by shorting a diode. This switch may be used to trigger a power off at the primary side from the secondary side. It could be used as an emergency shutoff if there is any fault at the secondary side.

These embodiments provide a significant improvement in reliability and safety over the prior art.

BRIEF DESCRIPTION OF THE DRAWINGS

In the following, the invention will be described by way of example, without limitation of the general inventive concept, on examples of embodiment and with reference to the drawings.

Figure 1:
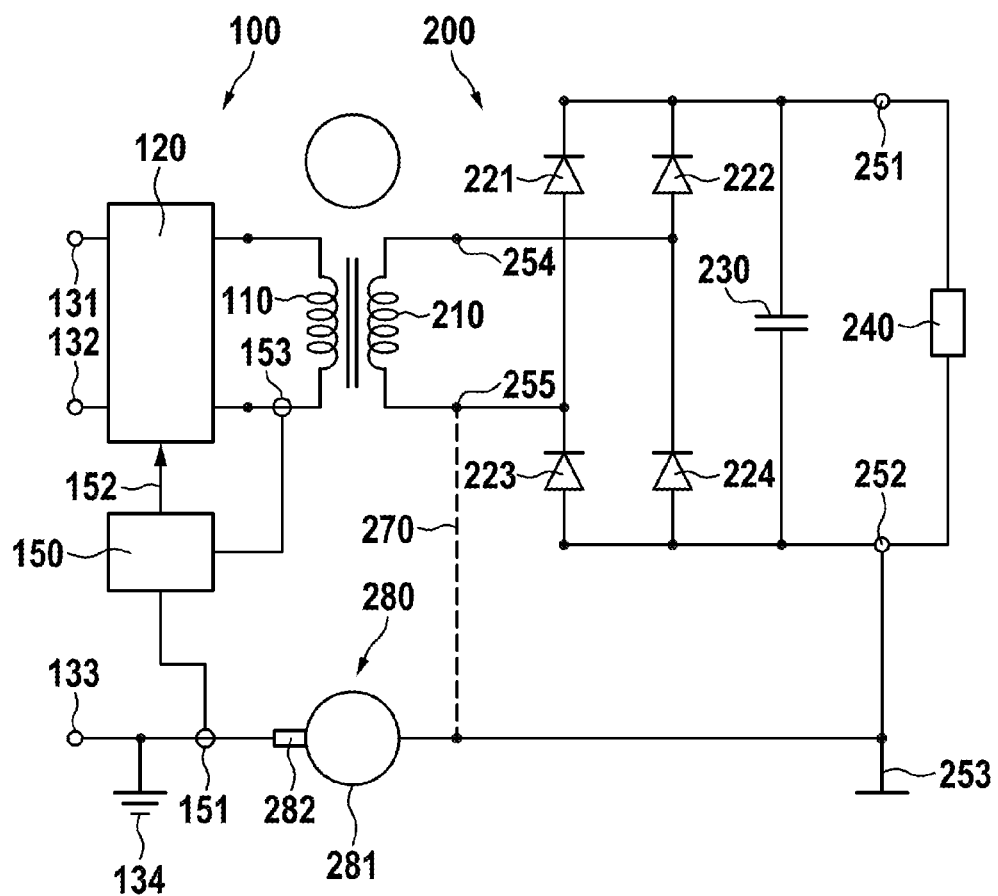
FIG. 1 shows a circuit diagram of a preferred embodiment.

Specific embodiments of the invention are shown by way of example in the drawings and will herein be described in detail, and are subject to modifications and alternative forms each of which is within the scope of the invention. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

In FIG. 1, a circuit diagram of a preferred embodiment is shown. An apparatus like a CT scanner may comprise a primary side 100 which preferably is stationary and a secondary side 200 which preferably is rotating. There is a rotating transformer having a primary winding 110 and a secondary winding 210 for inductively coupling electrical signals from the primary side 100 to the secondary side 200. The primary winding 110 is fed by an inverter 120 which converts input voltage received via primary inputs 131, 132 into an alternating voltage, preferably a voltage in a frequency range from between 1 kHz and 100 kHz, most preferably about 20 kHz. The voltage output of the secondary winding 210 is provided at secondary winding contacts 254, 255, which are connected to a rectifier. Preferably, the rectifier is a bridge rectifier comprising four diodes 221-224. The output of the rectifier preferably is connected to a filtering capacitor 230. Furthermore, connected to the filtering capacitor 230 may be a positive output voltage pin 251 and a negative output voltage pin 252, by which a load 240 may be connected. In a CT scanner, the load may comprise an X-ray tube and/or multiple electrical or electronic circuits, like a computer, a detector and imaging processing means. One of the output pins 251, 252 is connected to a secondary ground 253. Preferably, the negative output 252 is connected thereto. The secondary ground 253 is preferably based on mechanical parts at the rotating side, which may be the rotating part of a gantry of a CT scanner.

It is further preferred to have a slip ring 280 comprising at least one sliding track 281 and a at least one brush 282 for electrically connecting said secondary ground 253 to a protective earth 134 (which may be a primary ground), which may further be connected via a protective earth connector 133 to a main power system, or a specific ground pad.

It is further preferred to have a control unit 150 for controlling the inverter 120 or any other control means at the primary side. The controller 150 may be connected to a ground current sensor 151 for measuring a current between the secondary ground 253 and the protective earth 134. It may also measure a current through the primary winding 110, preferably by use of a second current sensor 153. Based on the measurement results, a trigger signal 152 may be generated.

In an inductive rotating coupler, certain faults may occur. One of these faults may be a short circuit of the secondary winding to the secondary ground 253. In this embodiment, a short circuit of the second secondary winding contact 255 is marked as a dashed line 270 indicating the short circuit. A similar scenario takes place, if the first secondary winding contact 254 has a short circuit to the secondary ground 253. There may also be a short circuit of any other part of the secondary winding 210 to secondary ground 253. By the short circuit, depending on the kind of short circuit, one of the rectifier diodes 221, 223 is shorted. The function is explained exemplarily by the kind of short circuit as indicated by dashed line 270. In this case, the rectifier diode 223 is shorted. As the rotating transformer is operated with an AC signal, it delivers positive and negative half waves at its output. When the secondary winding 210 delivers a positive output, where the voltage at the first secondary winding contact 254 is higher than the voltage at the second secondary winding contact 255, the circuit works as usual, as the rectifier diode 222 lets the current flow into the filtering capacitor 230 and the load 240. When a negative half wave is delivered, the voltage at the first secondary winding contact 254 is lower than the voltage at the second secondary winding contact 255, then the diode 224 provides a short circuit of the secondary winding. This short circuit leads to an asymmetrical current flow through the rotating transformer, which may easily be detected at the primary side, for example by second current sensor 153, but it would also generate a signal which may be detected by the ground current sensor 151 at the primary side.

Figure 4:
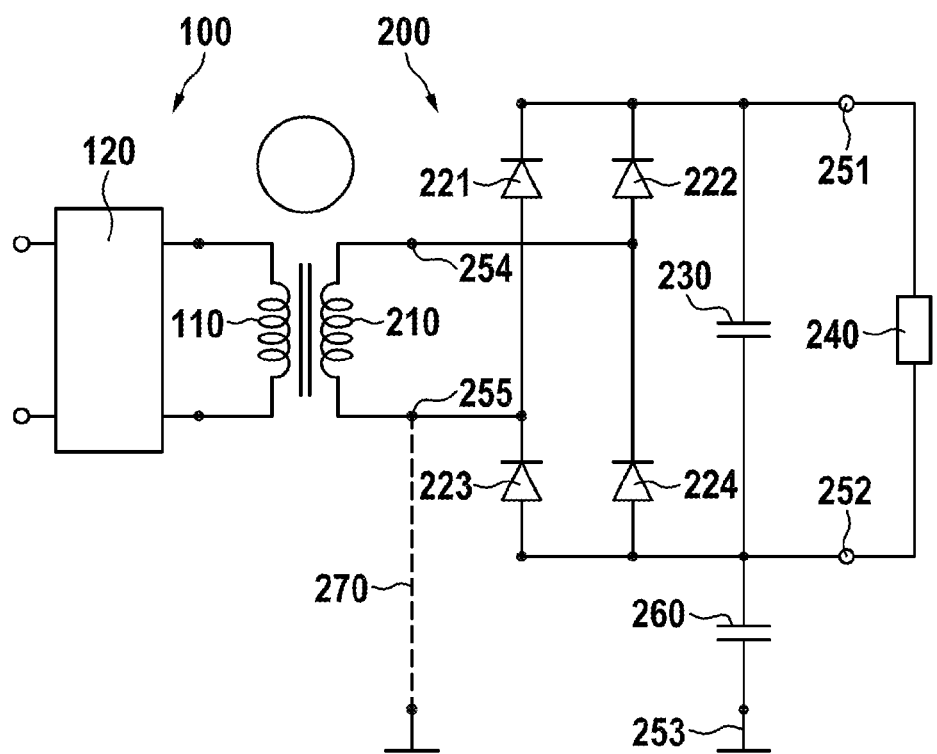
FIG. 4 shows a circuit known from the prior art.

Due to the asymmetrical short circuit of the secondary winding 210 by one of the rectifier diodes, it is impossible that the circuit works as a voltage doubler, as the prior art, as shown in FIG. 4.

Figure 2:
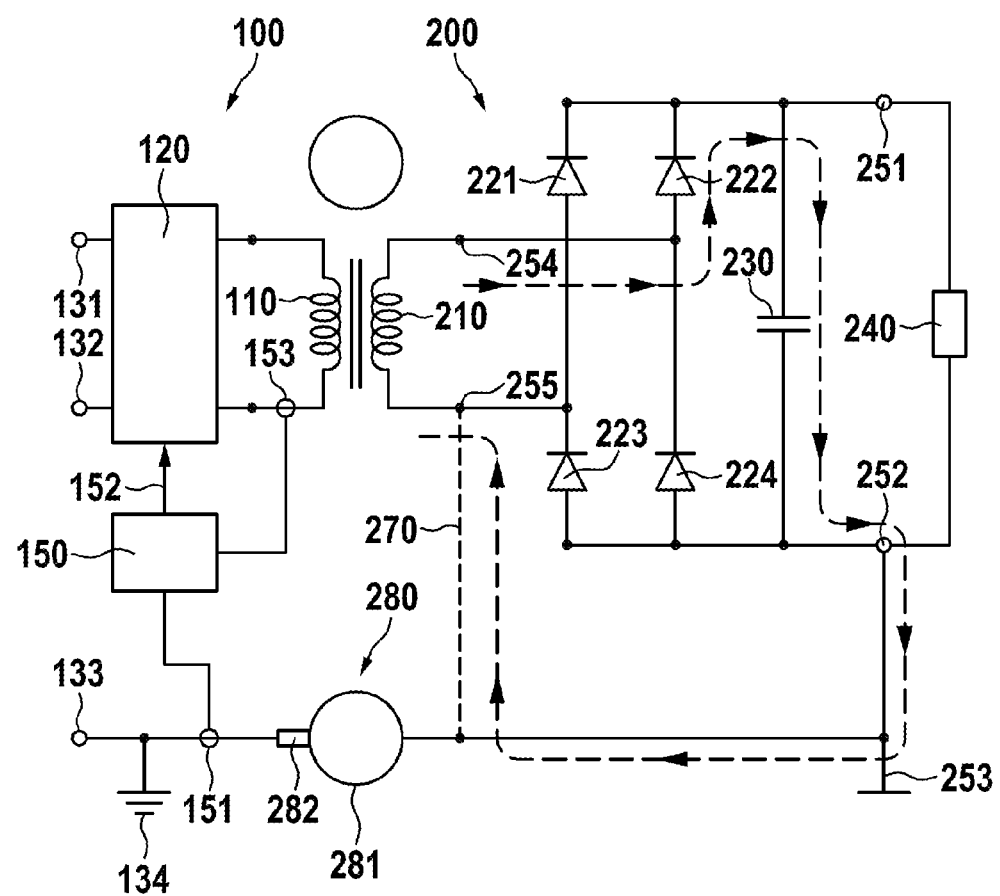
FIG. 2 shows the positive current path in a first failure mode in a first embodiment.

In FIG. 2, the positive current path in a first failure mode with a short circuit 270 is shown as a dashed line with arrows indicating the direction of the current. When the output voltage at the first secondary winding contact 254 is higher than the voltage at second secondary winding contact 255, then a current flows through the circuit as shown. It flows through a rectifier diode 222 into the capacitor 230 and back via secondary ground 253 and the short circuit 270 to the second secondary winding contact 255. This kind of current flow results in a normal charge of the capacitor 230.

Figure 3:
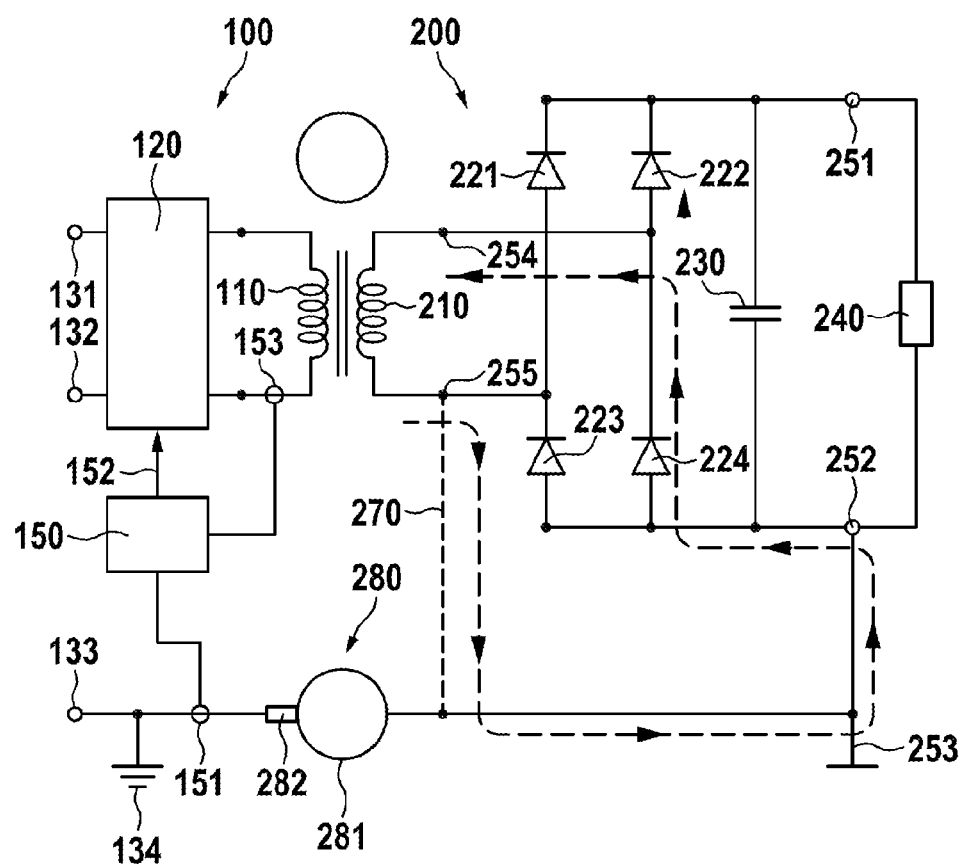
FIG. 3 shows the negative current path in a first failure mode in a first embodiment.

A negative current flow into the opposite direction, as indicated by FIG. 2 is shown in FIG. 3 by a dashed line with arrows indicating the direction of the current. The current flows from the second secondary winding contact 255 via the short circuit 270 and secondary ground 253 through diode 224 back to the first secondary winding contact 254. This is a short circuit via the diode 224 of the secondary winding 210. There are further parasitic capacitive currents flowing via the slip ring 280 to the protective earth 134 which may be detected by the control circuit 150. Furthermore, the asymmetrical load can easily be detected by a second current sensor 153 at the primary side of the inductive rotary joint.

In FIG. 4, an embodiment as known from the prior art is shown. Here, there is no slip ring 280 and no controller 150 with the associated circuits and components. Furthermore, there is a ground capacitor 260. This capacitor is required to provide a high frequency connection between the output of the circuit and the secondary ground 253. In this embodiment, the negative output of the power supply is connected to the secondary ground 253. If a short circuit between the secondary winding 210 and the secondary ground 253 occurs as indicated by dashed line 270, the circuit acts as a voltage doubler, causing approximately doubling of the regular output voltage at the capacitor 230. This would affect the operation of a connected load 240. There is a high probability that sensitive electronic components within the load may be destroyed or at least damaged.

Figure 5:
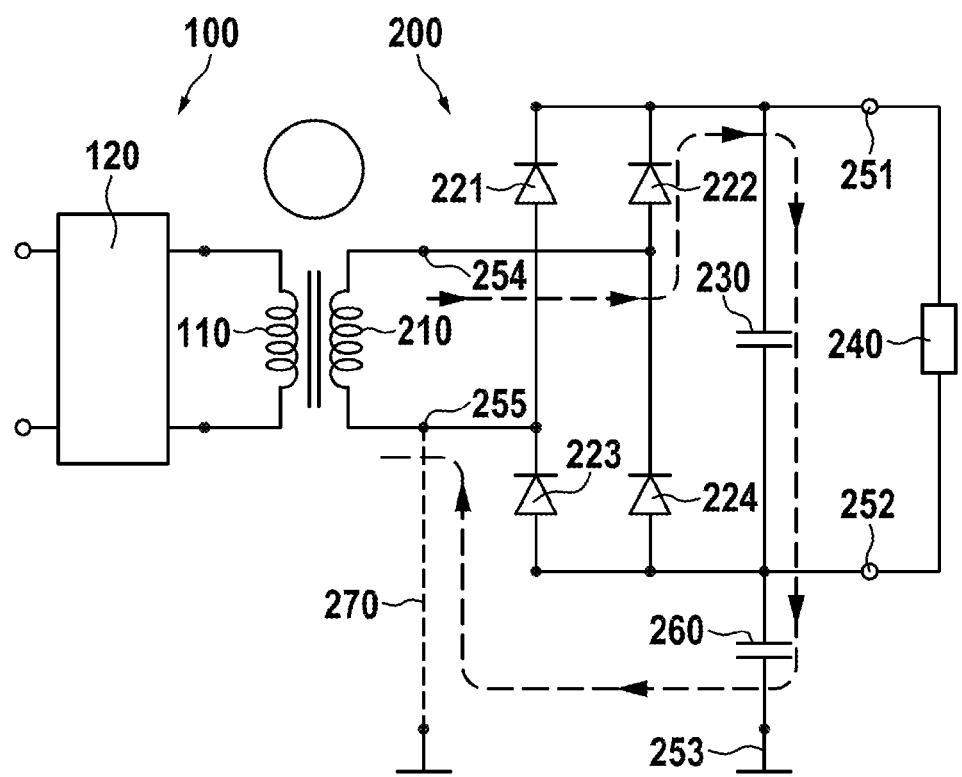
FIG. 5 shows the positive current path in a first failure mode according to prior art.

In FIG. 5, the positive current path in a first failure mode according to prior art is shown as a dashed line with arrows indicating the direction of the current. In the case of a positive output voltage of secondary winding 210, current is flowing through rectifier diode 222 into capacitor 230 and therefrom via capacitor 260, secondary ground 253, and the short circuit 270 back to the second secondary winding contact 255. As will be shown in the next Figure, the capacitor 260 was charged by a current of the preceding negative half wave output of secondary winding 210 to a negative voltage having the inverse polarity to the voltage at capacitor 230. Therefore, the ground capacitor's 260 positive side is at the secondary ground 253, whereas its negative side is at the negative output 252. As the total voltage over the capacitor 230 and the ground capacitor 260 equals to the output voltage of the secondary winding 210, the capacitor 230 must have twice the output voltage of the secondary winding 210. This leads to twice the output voltage at the load 240.

Figure 6:
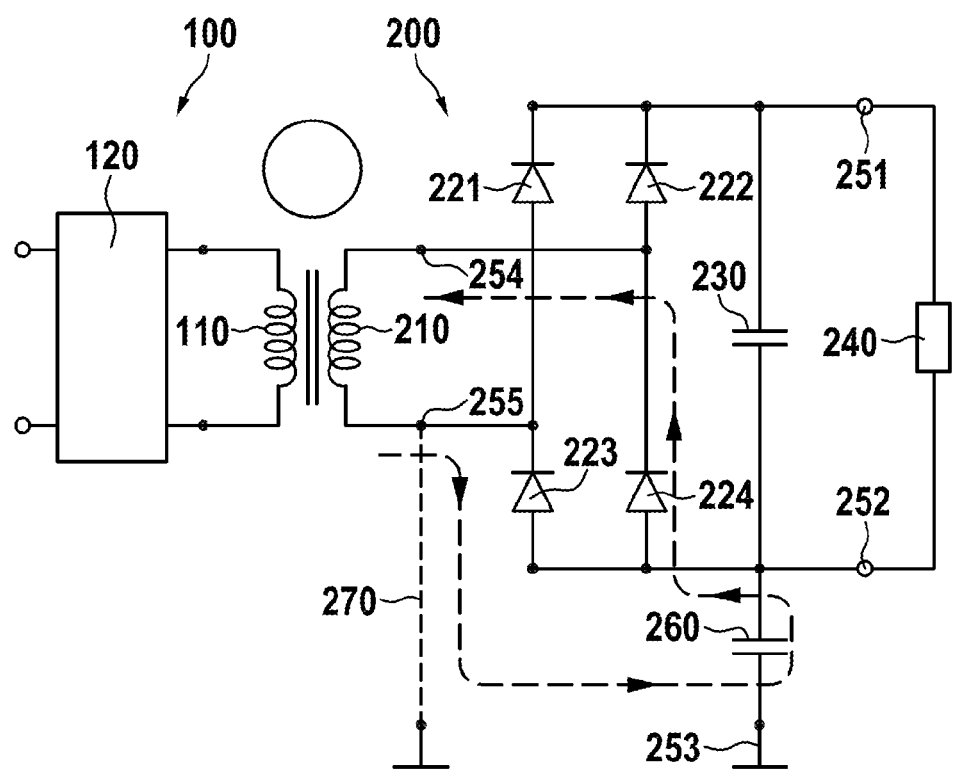
FIG. 6 shows the negative current path in a first failure mode according to prior art.

In FIG. 6, the current flow in a negative direction according to the prior art is shown as a dashed line with arrows indicating the direction of the current. The current flows from the second secondary winding contact 255 via short circuit 270 and secondary ground 253 through ground capacitor 260, and diode 224 back to the first secondary winding contact 254. It can be seen how the ground capacitor 260 is charged with a charge current in the opposite direction to capacitor 230, as mentioned in the description of the previous Figure.

Figure 7:
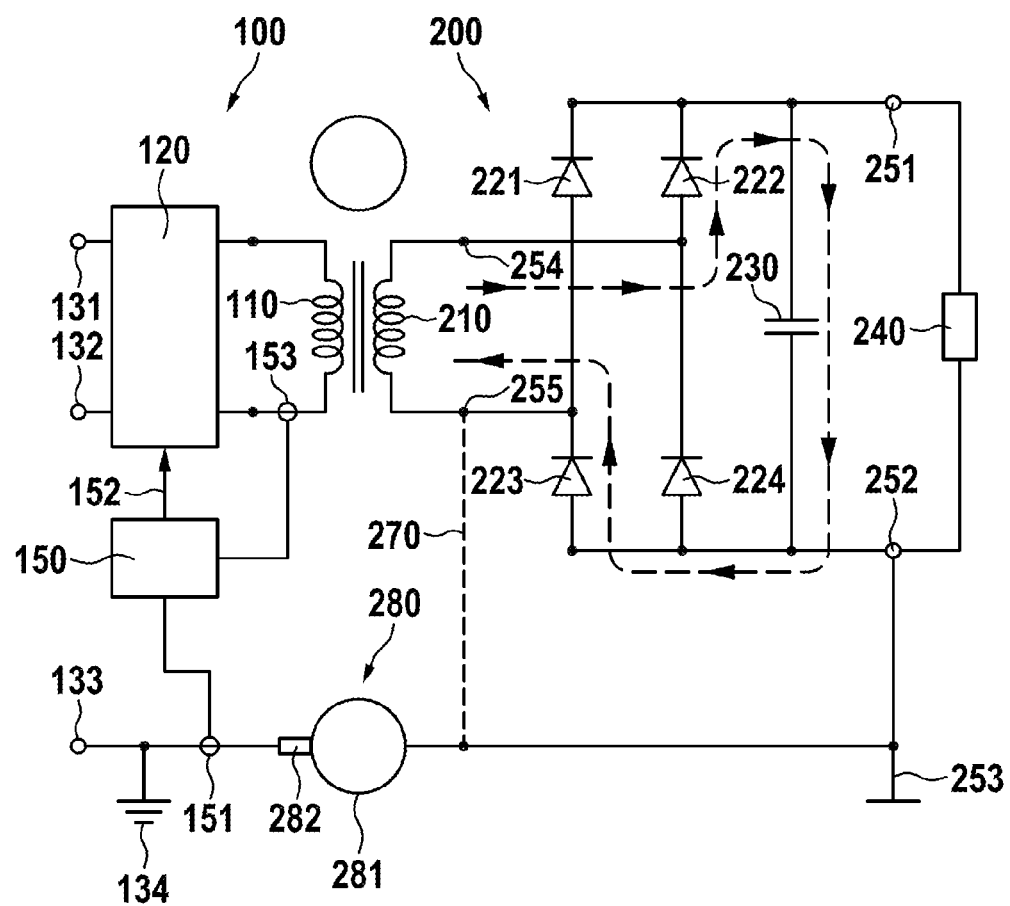
FIG. 7 shows the positive current flow in normal operation.

In FIG. 7, a positive current flow in normal operation of a preferred embodiment is shown. Here, the current flows from the first secondary winding contact 254 to diode 222, capacitor 230, and diode 223 back to the second secondary winding contact 255.

Figure 8:
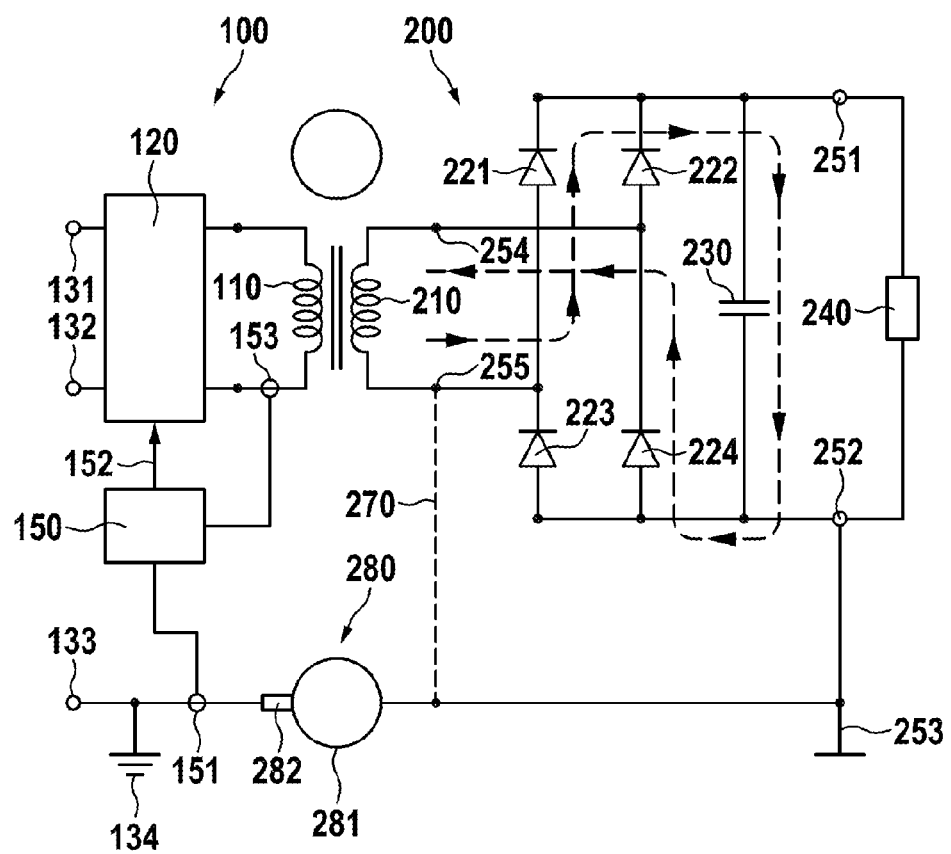
FIG. 8 shows the negative current flow in normal operation.

In FIG. 8, a negative current flow in normal operation of a preferred embodiment is shown. Here, the current flows from the second secondary winding contact 255 via diode 221, capacitor 230, and diode 224 back to the first secondary winding contact 254.

Figure 9:
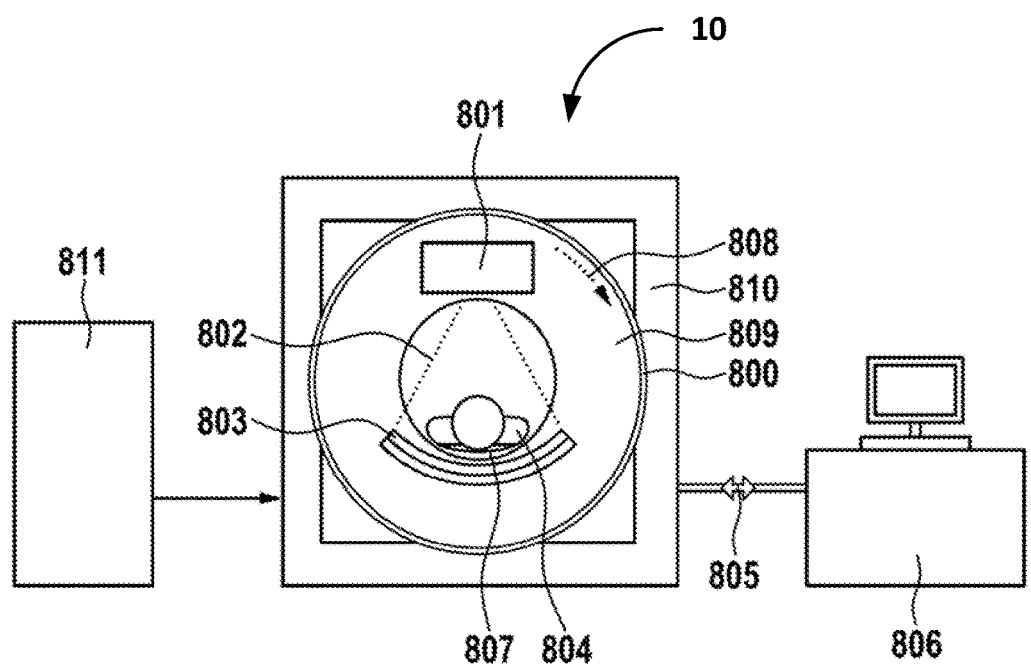
FIG. 9 shows a CT scanner.

FIG. 9 shows schematically a Computed Tomography (CT) scanner gantry 10. The stationary part is suspended within a massive frame 810. The rotating part 809 of the gantry 10 is rotatably mounted with respect to the stationary part and rotates along the rotation direction 808. The rotating part 809 may be a metal disk which supports an X-ray tube 801, an X-ray detector 803 and further electronic and mechanic components. This metal disk may define a secondary ground. The X-ray tube 801 is for generating an X-ray beam 802 that radiates throurth a patient 804 lying on a table 807 and which is intercepted by the X-ray detector 803 and converted to electrical signals and imaging data thereof. The imaging data obtained by the X-ray detector 803 are transmitted via a contactiess rotary joint (not shown) to an evaluation unit 806 by means of a data bus or network 805. Electrical power from a stationary power supply unit 811 may be transmitted by an inductive power coupler 800 to the rotating part 809.

Modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 primary side
110 primary winding
120 inverter
131, 132 primary input
133 protective earth connector
134 protective earth
150 control unit
151 ground current sensor
152 trigger signal
153 second current sensor
200 secondary side
210 secondary winding
221-224 rectifier diode
230 capacitor
240 load
251 positive output
252 negative output
253 secondary ground
254, 255 secondary winding contacts
260 ground capacitor
270 short circuit
280 slip ring 281 sliding track
282 brush
800 inductive power coupler
801 x-ray tube
802 x-ray beam
803 x-ray detector
804 patient
805 network
806 evaluation unit
807 patient table
808 rotation direction
809 rotating part
810 frame
811 power supply unit
10 Gantry

The invention claimed is:

1. An inductive power transfer circuit comprising:
   an inductive rotating coupler that has a primary side and a secondary side;
   wherein the primary side is rotatably arranged against the secondary side, one of the primary side and the secondary side being a rotating part of said inductive rotating coupler, another of the primary side and the secondary side being a stationary part of said inductive rotating coupler;
   wherein the primary side includes at least a primary winding and a protective earth having a galvanic contact;
   wherein the secondary side includes at least a secondary winding;
   a rectifier connected to the secondary side; and
   a capacitor connected to the rectifier;
   wherein the secondary side further having a positive output and a negative output configured to deliver a DC voltage to a load at the secondary side;
   wherein one of the positive output and the negative output is connected to a secondary ground at the rotating part, which is further coupled via the galvanic contact to the protective earth at the primary side.

2. An inductive power transfer circuit according to claim 1, wherein the galvanic contact comprises at least a slip ring that includes at least one sliding track and at least one brush sliding at the at least one sliding track.

3. An inductive power transfer circuit according to claim 1, wherein the galvanic contact comprises at least a bearing between the secondary side and the primary side.

4. An inductive power transfer circuit according to claim 1, wherein the rectifier is a bridge rectifier.

5. An inductive power transfer circuit according to claim 1, further comprising
   an inverter configured to drive the primary winding.

6. An inductive power transfer circuit according to claim 1, further comprising:
   a control circuit at the primary side, the control circuit being configured to detect at least a short circuit between the at least secondary winding and the secondary ground.

7. An inductive power transfer circuit according to claim 6, further comprising:
   an inverter configured to drive the primary winding;
   wherein the control circuit is configured to provide a trigger signal for disabling the inverter.

8. An inductive power transfer circuit according to claim 6, wherein the control circuit has at least one ground current sensor configured to measure a current through a slip ring of the galvanic contact or at least one sensor configured to measure an input current at a primary input for measuring the current through the primary winding.

9. An inductive power transfer circuit according to claim 1,
   wherein rectifier comprises diodes; and
   wherein the inductive power transfer circuit further comprises a switch configured to generate a short circuit of the diodes of the rectifier.

10. A CT scanner comprising:
    an inductive power transfer circuit that includes:
        an inductive rotating coupler that has a primary side and a secondary side, the primary side being rotatably arranged against the secondary side, the primary side being a stationary part and the secondary side being a rotating part;
        wherein the primary side includes at least a primary winding and a protective earth having a galvanic contact;
        wherein the secondary side includes at least a secondary winding and a secondary ground;
        a rectifier connected to the secondary side; and
        a capacitor connected to the rectifier;
        wherein the secondary side further having a positive output and a negative output configured to deliver a DC voltage to a load at the secondary side;
        wherein one of the positive output and the negative output is connected to the secondary ground, which is further coupled via the galvanic contact to the protective earth.

* * * * *